United States Patent [19]

Padden

[11] Patent Number: 4,747,315

[45] Date of Patent: May 31, 1988

[54] FLUID SAMPLING

[76] Inventor: Harvey F. Padden, 5 Iron Forge Village South, Pompton Lakes, N.J. 07442

[21] Appl. No.: 500,809

[22] Filed: Jun. 3, 1983

Related U.S. Application Data

[62] Division of Ser. No. 201,823, Oct. 29, 1980, Pat. No. 4,432,248.

[51] Int. Cl.⁴ .......................................... G01N 35/00
[52] U.S. Cl. ................................................ 73/863.01
[58] Field of Search ........... 73/863.01, 863.02, 863.03; 417/44, 45, 280

[56] References Cited

U.S. PATENT DOCUMENTS

| | | | |
|---|---|---|---|
| 3,274,939 | 9/1966 | Foster | 417/33 |
| 3,953,152 | 4/1976 | Sipin | 417/45 |
| 4,024,864 | 5/1977 | Davies | 417/45 |
| 4,237,451 | 2/1980 | Hollenbeck | 417/45 |
| 4,420,787 | 12/1983 | Thomas et al. | 417/45 |

Primary Examiner—Stewart J. Levy
Attorney, Agent, or Firm—Hymen Diamond

[57] ABSTRACT

A fluid sampler in which the flow of the fluid in the fluid processor is maintained constant. The fluid is transmitted by a motor-driven pump. The motor circuit includes feedback means which contains no moving parts and which responds to the loading on the motor for maintaining the flow of fluid constant.

25 Claims, 6 Drawing Sheets

FLUID SAMPLING

REFERENCE TO RELATED APPLICATION

This patent is a division of Ser. No. 201,823 filed 10/29/80, now U.S. Pat. No. 4,432,248, granted Feb. 21, 1984 to Hill S. Lalin for FLUID SAMPLING and assigned to Gilian Instrument Corporation. U.S. Pat. No. 4,432,248 is herein referred to as parent patent.

BACKGROUND OF THE INVENTION

This invention relates to fluid sampling and has particular relationship to the sampling of gases, predominantly air, for selected components. Typically, the fluid sampling with which this invention concerns itself is the sampling of air in plants for harmful components pursuant to the Occupational Safety and Health Act (OSHA) or the sampling of the air at a site such as Love Canal contaminated by chemical waste. Sampling of this type is typically carried by a sampler carried or "worn by" the person subjected to the harmful components in the air. The sampling may be carried out throughout the working day of the personnel involved or during measured intervals. On occasion, it is also desirable that the flow of air through the sampler be limited.

A sampler includes a pump which pumps the air through a channel including the collecting or processing device which collects and/or measures the concentration of the harmful components. The processing device is usually interposed in the inlet (suction side) to the pump; it may also be in the outlet (pressure side) particularly in the case of bag collection of chemicals. The components sampled are gases or vapors or solid particulate. The air sampled contains dirt such as dust and other debris and it is necessary that such dirt be filtered out prior to entering the pump. The pump is protected by a so-called pump filter through which the pumped air flows as it is drawn into the channel. The function of the pump filter is to protect the pump from this dirt and debris. The filter becomes loaded with dirt during operation and presents an increasing pressure increment to the pump. In addition, there is an increasing impedance to the flow of pumped air through the channel and the flow or the time rate of the flow of air decreases unless the effect of the filter on the flow is compensated. The flow may also vary for other reasons than accumulation of dirt on the filter. In accordance with the teachings of the prior art, a differential pressure switch is interposed in the outlet of the flow channel to suppress the variation of the air flow. This pressure switch responds to the differential between the pressure in a chamber and the pressure outside of the chamber. The chamber is connected to the region outside through a needle valve. The pressure switch opens and closes repeatedly responsive to the pulsations produced by the pumping. One disadvantage of this expedient is that the repeated operation of the pressure switch has a tendency to cause fatigue in its linkages. Another, and more important, disadvantage is that traces of contaminents such as dirt clog and impede the operation of the needle valve precluding satisfactory, stable and reliable response of the switch to pressure variations in the flow channel. Another drawback is that additional pumping power is required to maintain the pressure required for sensing because an increment of pressure is absorbed for maintaining the control power.

It is an object of this invention to overcome the disadvantages of the prior art and to provide a fluid sampler which shall not include moving parts subject to fatigue and which shall operate reliably and with stability to maintain flow of fluid being sampled substantially constant.

SUMMARY OF THE INVENTION

An aspect of this invention arises from the realization that variation in the flow through the sampler varies the pressure differential; i.e., the difference in pressure between the outlet from and the inlet to the pump, which is herein referred to as $\Delta P$, and the $\Delta P$ varies the loading on the motor which drives the pump. In accordance with this invention, the motor is controlled responsive to its loading; i.e., to $\Delta P$, in such a manner as to maintain the flow through the sampler substantially constant over its operating range of flow. The sampler has an electronic solid-state control which includes a flow compensation control, a battery check, a battery low-voltage indicator, a low-flow indicator, a timer and an on-off switch.

The flow compensation control provides for constant air flow from the pump at any preset flow over range of operation of the sampler, typically between 500 milliliters and 4 liters per minute. The compensation control is effective because of the linearity of the pump incorporating the pre-loaded valving disclosed in Lalin Application. The compensation control includes a sensing resistor mounted in the motor leg which provides a voltage signal proportional to the motor-load current to the power supply which in turn adjusts the motor voltage proportionately to the pump-load-line curves thereby maintaining relatively constant flow over a back pressure range typically from 0 to 40 inches of water (positive or negative) at flow rates over the operating range. Additional features are automatic pump shutdown and fault indication should the pump be restricted (suction or discharge) beyond its operating range.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings in which:

FIGS. 5 and 6 show the magnitudes and types of the components incorporated in an embodiment of this invention which operates satisfactorily. This data is included in FIGS. 5 and 6 for the purpose of aiding those skilled in the art in practicing this invention, as

DETAILED DESCRIPTION OF EMBODIMENT

Figure 5:
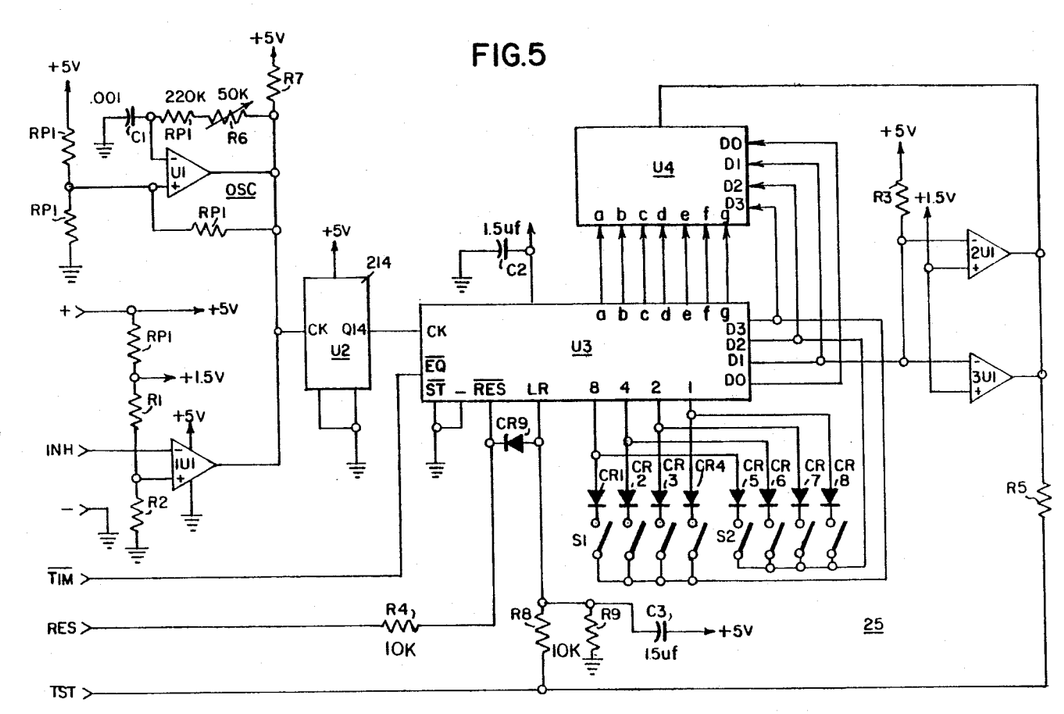
FIG. 5 is a schematic showing the timing network incorporated in this invention.
Figure 6:
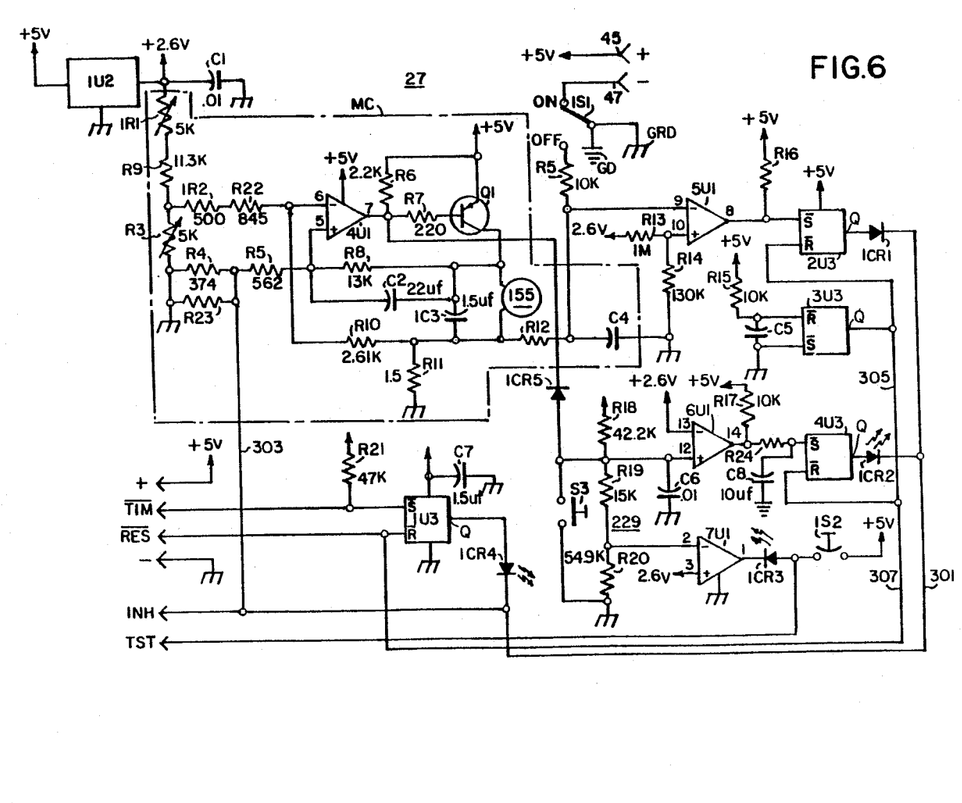
FIG. 6 is a schematic showing the control incorporated in this invention.

The apparatus shown in the drawings is a sampler 20 including a pneumatic assembly 212, a battery pack 23, a board 25 containing the timing network (FIG. 5) on a printed circuit and a board 27 containing the control network (FIG. 6) on a printed circuit. The sampler 20 has a casing including a front case 29 and a rear case 31. The battery pack 23 is a cartridge including a battery 33 in a container 35. The front case 29 includes a frame-like recess 37 on the left (with reference to FIG. 1) and a slot 39 on the right. The timing-network board 25 and the control-network board 27, include conductors that are interconnected (FIGS. 5 and 6). The boards 25 and 27 are coextensive vertically (with reference to FIG. 1). The planar unit formed by the boards 25, 27 is on bosses (not shown) extending from the back of recess 37. The battery pack 23 is mounted behind the boards 25 and 27 with the battery 33 contiguous to the boards and the socket receptacles 41 and 43 of the battery connected to terminals or pins 45 and 47 (FIG. 6) of the control network 27. A nameplate 49 is mounted in the recess 37 abutting the recess. A cover 51 extends into the recess 37 flush with the outer rim of the front case 29 and abuts the nameplate 49. The cover 51 has tongues 53 which engage cooperative grooves (not shown) in the top of recess 37.

The pneumatic assembly 21 is supported in the right-hand compartment (with reference to FIG. 1) of the front case 29. A flowmeter 55 in the pneumatic assembly 21 is disposed oppositely the slot 39. A window 57 extends into the slot 39 between the flowmeter 55 and the slot with its offset frame abutting the boundaries of the slot 39.

Figure 1:
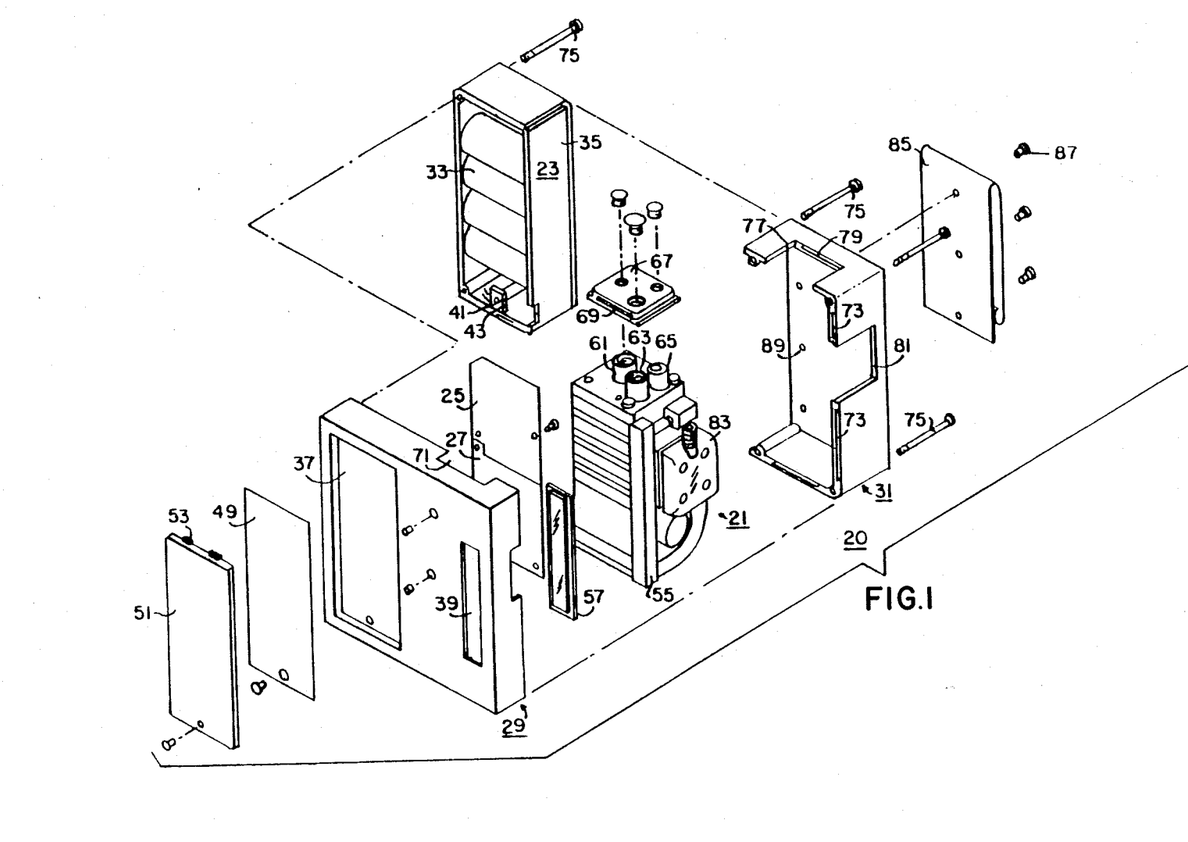
FIG. 1 is an exploded view in isometric of an embodiment of this invention.

The top of the pneumatic assembly 21 has hollow bosses 61, 63 and 65. An insert 67 is disposed on the top extending over the bosses 61–65. The insert 67 has a tongue 69 which engages a groove (not shown) in the edge of a slot 71 in the top of the front case. The rear case 31 encompasses the pneumatic assembly 21, its inner edge engaging the inner edge of the front case. The inner edge of the rear case is provided with tongues 73 which engage slots (not shown) in the inner edge of the front case. The rear case 31 is secured by screws 75 through bosses in its four corners to the front case 29. The rear case has a slot 77 in its top in which it engages the insert 67. The inner edge of the slot 77 has a groove 79 which is interlocked with a tongue (not shown) in the insert 67. In its side the rear case has a slot 81 which encompasses the inner boundary of the pump filter assembly 83.

A belt clip 85 is secured by rivets 87 which pass through holes 89 near the left-hand edge of the rear case 31. The belt clip 85 extends over this left-hand edge defining a vertical space or pocket for receiving the battery pack 23.

The manner in which the sampler 20 is assembled is disclosed in detail in parent patent. Outside dimensions of a typical sampler is also disclosed in parent patent.

Figure 3:
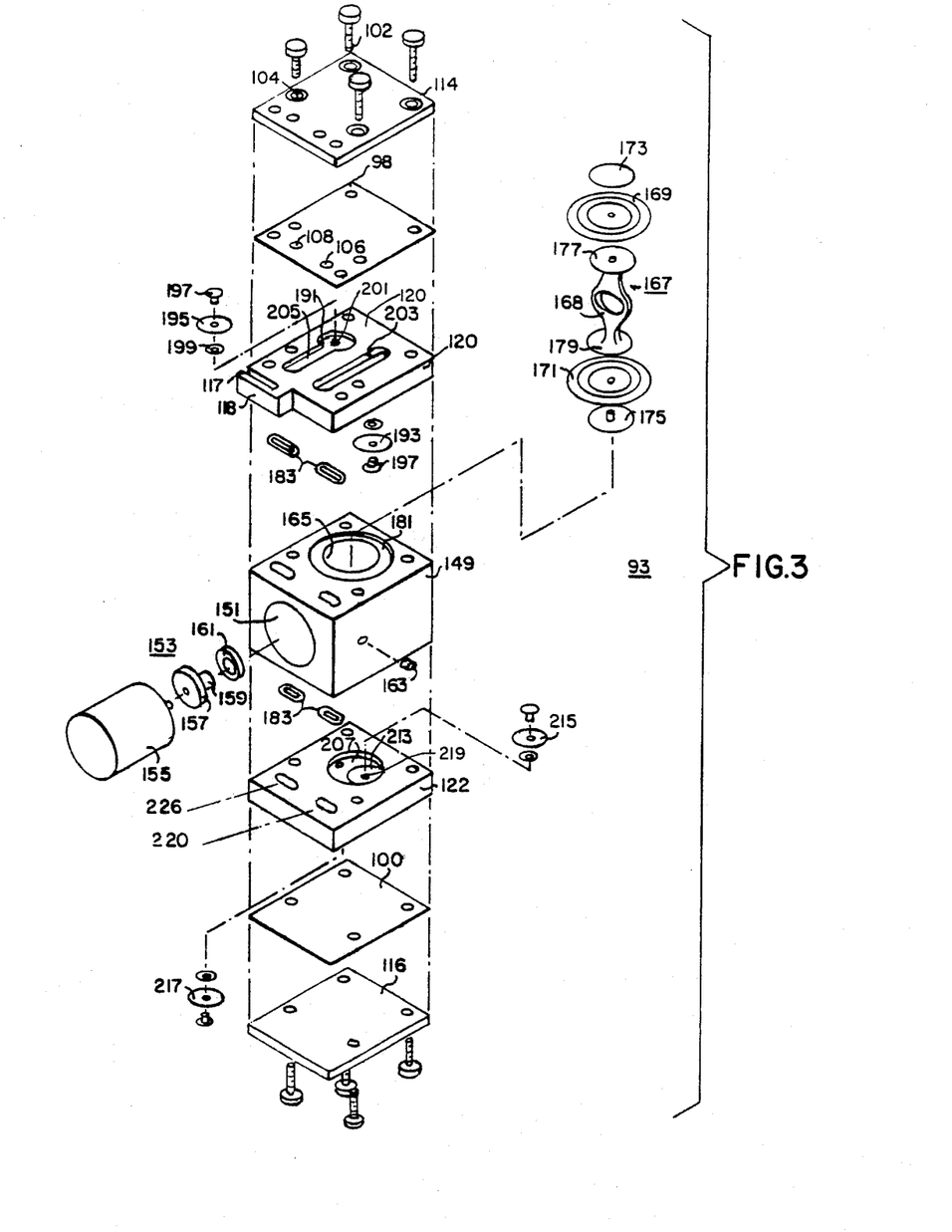
FIG 3 is an exploded view in isometric showing the pump incorporated in the embodiment of this invention shown in FIG. 1.
Figure 4:
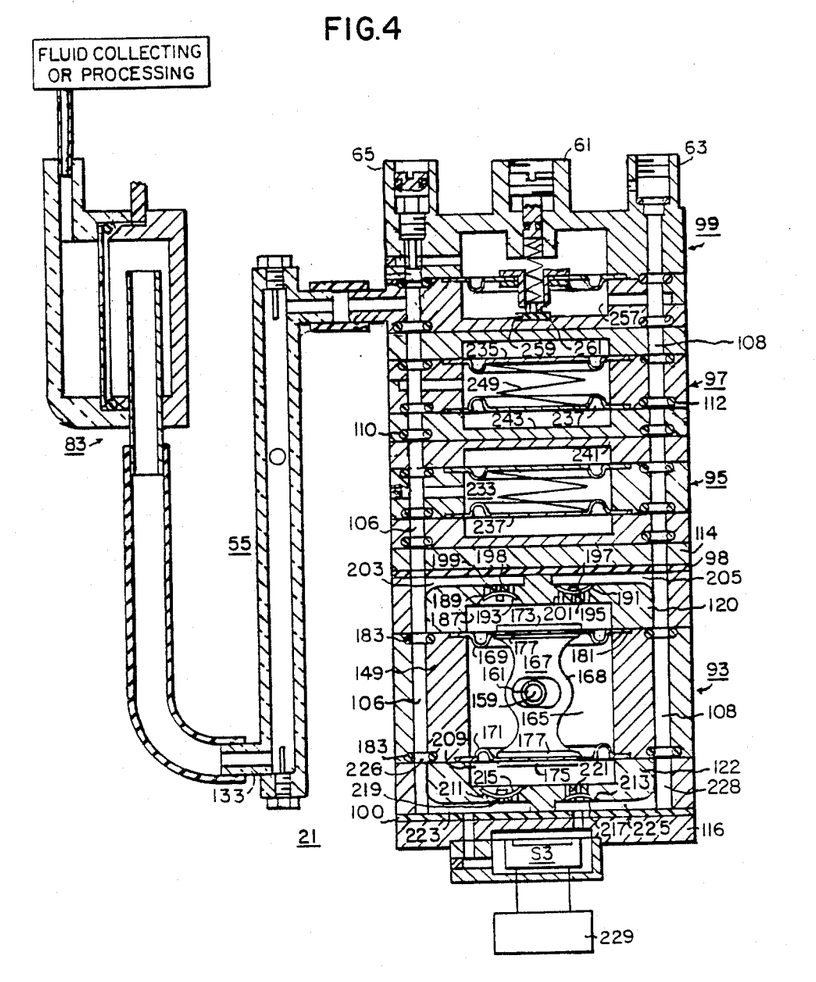
FIG. 4 is a view in longitudinal section, partly diagrammatic, of the pneumatic assembly with the section planes displaced transversely with reference to each other to facilitate the understanding of this invention.

The pneumatic assembly 21 (FIG. 4) includes in addition to the flowmeter (ROTOMETER) 55 and the pump filter 83, the pump assembly 93, damper assemblies 95 and 97 (FIG. 4) and regulator 99. The pump 93, dampers 95 and 97, and regulator are stacked and secured together by screws. In the stack are included gaskets 98 and 100 (FIGS. 3, 4) between the top plate 114 and the upper valve plate 120 and between the bottom plate 116 and the lower valve plate 122 of the pump assembly 93. Each assembly 93, 95, 97 and 99 is held together by screws 102 (FIG. 3) countersunk in holes 104. The pump 93 and the dampers 95 and 97 and regulator 99 have coextensive openings which, when these components are stacked, form a suction channel 106 (FIG. 4) through which air is sucked into the pneumatic assembly 21 by the pump. The components 93, 95, 97 and 99 also have openings which form the exhaust channel 108 through which air is exhausted from the pneumatic assembly when these components are stacked. As shown in FIG. 4, the channel 106 is coaxial with boss 65 and the channel 108 with boss 63. The openings in the pump, dampers, and regulator which form channels 106 and 108 are sealed by O-rings 110 and 112 compressed between each pair of abutting components 93 and 95, 95 and 97, and 97 and 99.

The pump (FIG. 3) includes a body 149, in the form of a rectangular parallelapiped, in addition to the top valve plate 120, the bottom valve plate 122, the top plate 114, the bottom plate 116 and the gaskets 98 and 100. The body 149 has a horizontal cavity 151 into which an eccentric drive 153 extends. This drive includes a motor 155 and an eccentric 157 driven by the motor 155. The eccentric 157 has an eccentrically disposed pin 159 which is rotatable in a bearing 161. The motor 155 is secured in the cavity 151 by a set screw 163.

The body 149 also has a vertical bore 165 which extends through the top and bottom of the body 149 and is in communication with the cavity 151. Within the vertical bore 165, a diaphragm assembly 167 is mounted. This assembly 167 includes a yoake 168, upper and lower diaphragms 169 and 171 and diaphragm retainers 173 and 175. The diaphragms 169 and 171 are held in engagement with end plates 177 and 179 of the yoke 168 by the retainers 173 and 175. The diaphragms 169 and 171 are seated in annular recesses 181 (FIG. 3) in the top and bottom of the body 149. They are secured in these recesses by the top plate 120 and the bottom plate 122. The pin 159 and bearing 161 extend into the opening in the yoke 168 with bearing 161 engaging the surface bounding the opening. As the pin is rotated by motor 155, the yoke 168 is moved upwardly and downwardly correspondingly flexing diaphragms 169 and 171 upwardly and downwardly in opposite phase. There are O-ring seals 183 (FIGS. 3, 4) between the body 149 and the upper and lower valve plates 120 and 122 which seal the bore 165.

The upper valve plate 120 has a circular opening opposite to and sealed by the diaphragm 169. The diaphragm 169 and the upper valve plate 120 at the opening form a plenum 187 (FIG. 4). The base of this plenum in the upper valve plate has disk shaped cavities or valve-seats 189 and 191 (FIG. 4). In each cavity, a pre-stressed valve plate 193 and 195 (best seen in FIG. 4) is seated. Each valve plate is secured in the cavity and pre-stressed by a retainer 197 which engages a spacer 198 (FIG. 4) on the opposite side of the valve plate. There are holes 199 and 201 in the seats 189 and 191; hole 199 connecting the plenum 187 to the suction cahnnel 106 and hole 201 connecting the plenum to the exhaust channel 108. This connection is through a slot 203 and key-shaped slot 205 in the upper valve plate 120. The valve plate 193 is positioned so as to disengage its seat 189 when the diaphragm 169 moves downwardly creating a partial vacuum in plenum 187. For this setting of the diaphragm the other valve plate 195 is urged into tighter engagement with its seat 191. Conversely, when diaphragm 169 is moved upwardly increasing the pressure in plenum 187, valve plate 195 opens and valve plate 193 closes more tightly.

The lower valve plate 122 likewise has a circular hole 207 (FIG. 3) which is sealed by diaphragm 171 to form plenum 209 (FIG. 4). The base of plenum 209 has disk-shaped valve seats 211 and 213 on which valve plates 215 and 217 are seated. The seats have holes 219 and 221 connecting the plenum to suction channel 106 through slot 223 (FIG. 4) and to the exhaust channel 108 through slot 225. The body 149 is connected to the suction channel 106 and the exhaust channel 108 through oval slots 226 and 228 which are sealed by O-rings 183.

A pressure switch S3 (FIGS. 4, 6) is suspended from the bottom plate 116. This switch S3 is in communication with the suction slot 223 on one side and with the exhaust slot 225 on the opposite side and responds both to excessive vacuum on the suction side and to excessive pressure on the exhaust side to actuate a latch 4U3 (FIG. 6) to stop operation under conditions requiring such stopping, for example, when a suction or exhaust line is plugged. The switch S3 acts as back-up for the electrical protective apparatus. The structure and operation of the damper 95, 97 and the regulator 99 and their cooperation with pump 93 are disclosed in detail in parent patent.

The pneumatic assembly 21 is controlled electrically by the timer board 25 and the control board 27. Actual networks which operate satisfactorily are shown in the schematics, FIG. 5 for the timer, and FIG. 6 for the control network. In these networks, integrated circuits are to a large extent included. For example, operational amplifiers U1-3U1 are part of a 339 integrated circuit. The labeling is not included in FIGS. 5 and 6. The actual magnitudes of components are shown. Where the magnitude of a capacitor is shown as a number along, for example, .001 for capacitor C1, FIG. 5, the capacity is in micro-microfarads (piko farads). Magnitudes in microfarads are so labeled. Resistor magnitudes are in ohms, in thousands of ohms where a number is followed by a "K", in millions of ohms where a number is followed by an "M". To a large extent, input and output signal magnitudes are referred to digitally as 1 or 0, instead of high and low. A 1 is a voltage of 2.4 volts and higher; a 0 is 0.4 volts and lower. However, on occasion, an intermediate state exists at about 2.5 volts at which certain operation is enabled. Output on the control board 27 and inputs to the timer board 25 are labeled T1M, etc. A bar over an input, for example $\overline{T1M}$, means that a 0 is impressed to produce the required operation. Where a bar is absent, for example INH, a 1 is impressed to produce the required operation, reset in this case. Since the container of the sampler is composed of an electrical insulator, grounding is provided by conductors on the printed circuit boards 25 and 27. Power grounding is represented conventionally by three lines GR of decreasing length. Digital grounding is represented by a forklike symbol GRD.

The apparatus as shown in FIG. 5 includes an oscillator OSC, a frequency divider U2, typically 14 stages (divides by $10^{14}$), a counter U3 and a display U4. The oscillator OSC includes the operational amplifier U1, the calibration resistor R6, the resistors RP1 and the capacitor C1. Its period, typically is about 366 microseconds. The output of the oscillator OSC is impressed on the clock input CK of the divider U2. At its output Q14, the divider U2 produces a low frequency signal, typically 1 cycle every 6 seconds. This signal is impressed on the clock input CK of the counter U3. The number of counts which the counter produces is preset by the selector switches S1 and S2. S1 sets the counts in hundreds and S2 in tens. The switches operate through diodes CR1 through CR8. Counter U3 includes a register and a comparator (neither shown).

Figure 2:
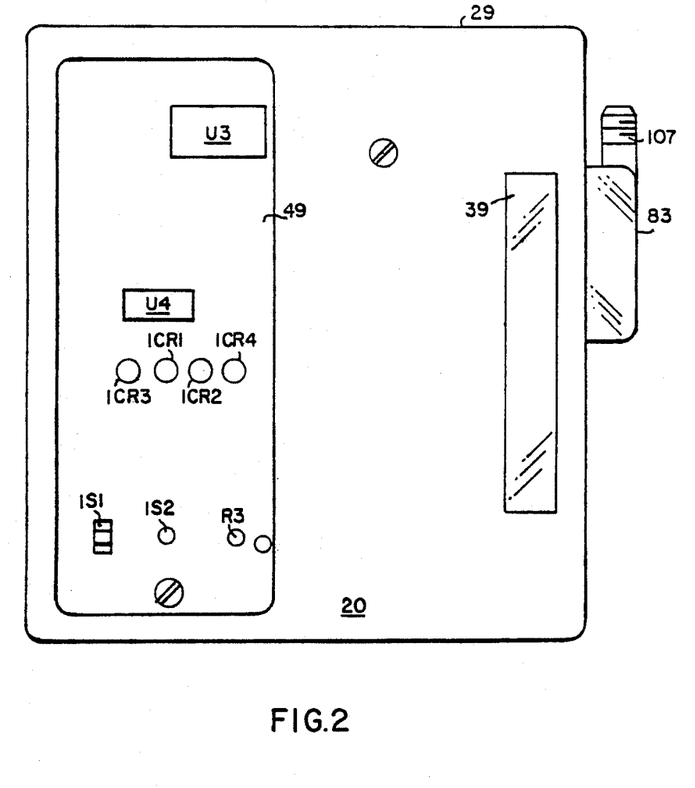
FIG. 2 is a view in front elevation of this embodiment with the cover over the name plate removed.

At the start of an operation when power is first applied with switch 1S1 set to ON, input LR of U3 goes to 1 from the 5 volt supply through capacitor C3. As capacitor C3 charges up, input LR goes to 2.5 volts. Ultimately, capacitor C3 is fully charged and LR becomes 0. When LR goes to 1 (5 volts), the number set by the switches S1 and S2 is loaded in the register of U3. The reset output $\overline{RES}$ is set to 0 and the counting starts after LR goes to 2.5 volts. The counting continues with LR 2.5 volts or lower. When the comparator finds the input count to be equal to the count stored in the register, $\overline{EQ}$ goes to 0, latch 1U3 (FIG. 6) is set producing a 1 at INH, inhibit. The output of amplifier 1U1 goes to 0, stopping oscillator OSC to stop the counting. Also, the motor 155 (FIG. 6) is stopped. In each latch, such as 1U3 (FIG. 6), a setting produced by a 0 at $\overline{S}$ is latched in and remains latched in after the 0 is removed from $\overline{S}$ until a 0 is impressed on $\overline{R}$ to reset the latch. With LR at 1 at the start, the display U4 is blanked. A signal on TST produced by closing switch 1S2 (FIGS. 2, 6) enables the display U4. The display is impressed from counter U3 on display U4 through outputs a through g of U3 and inputs a through g of U4. Outputs D0 through D3 of U3 transfers the digits of the display through input D0 through D3 of U4. D3 is the most significant digit and the D0 the least significant digit. The decimal point is derived through operational amplifiers 2U1 and 3U1, with TST, test, at 1. When D1 is 1, there is no decimal point. With D1 at 0, there is a decimal point.

FIG. 6 shows the motor control MC for motor 155 in the dash-dot block. The remainder of FIG. 6 shows the indicating and protective circuit. The apparatus shown in FIG. 6 includes regulator 1U2 which produces a reference voltage at its output. Typically, the output is 2.6 V for any battery voltage above 4.3 volts. The 2.6 reference voltage is impressed at selected points in the circuit shown in FIG. 6.

The motor control MC responds to the loading on the motor to maintain the flow of air; i.e., liters or milliliters per minute, constant, as the air is pumped by pump 93 through the pneumatic system. In this control, the motor 155 is supplied through the transistor Q1. The motor current flows in a circuit extending from the +5-volt terminal of the battery 33, through the emitter and collector of Q1, the motor, resistor R11 to ground. The current through resistor R11 is substantially equal to the motor current. The filter R12-C4 introduces a delay into the control to prevent undesired tripping of the overcurrent detector circuit for transients. The capacitor 103 across the motor suppresses brush noise. The apparatus is energized with switch 1S1 in the "ON" position. With 1S1 in the "OFF" position, C4 discharges to ground. Transistor Q1 is controlled by operational amplifier 4U1 whose output is connected to the base of Q1 through resistor R7. Resistor R6 between the emitter of Q1 and the output of 4U1 assures that when Q1 is to be cut off, it is completely cut off. There is a feedback network between the collector of Q1 and the positive input (pin 5) of 4U1. This network includes resistor R8 and network R4, R23, and R5. R23 is a thermister whose resistance varies exponentially with temperature; R4 linearizes the response of R23. The network R4, R23, R5 varies in resistance proportionately to change in temperature and compensates for the variation of the resistance with temperature of the copper in motor 155. Capacitor C2 introduces a delay of 0.3 sec in the response of the control to changes in the loading; i.e., the air flow. The network R8 and R4, R5 R23 sets the gain of the amplifier unit 4U1-Q1.

The control for the amplifier unit is impressed on the negative input of 4U1 from the 2.6 volt output of 1U2 through the network 1R1, R9, 1R2, R22, R10, R11 and R3. The drop across R11 which measures the motor current is compared to the voltage derived through resistors 1R1, R9, 1R2, R22 and R3. R3 sets the desired air flow, 1R1 is adjusted for compensation at the high end, and 1R2 for compensation at the low end.

The circuit disclosed is able to track the changes in flow without becoming unstable. As the flow varies, the drop through R11 changes compensating for the flow change by changing the terminal voltage supplied to the motor. If the flow is increased above the set magnitude, the drop across resistor R11 decreases decreasing the terminal voltage across the motor; if the flow decreases below the set magnitude, the drop across resistor R11 increases, increasing the terminal voltage.

When the comparator in U3 signals the end of a count and there is a 0 on $\overline{EQ}$, entered count equals preset register count, there is a 0 on $\overline{TIM}$. Latch 1U3 is set at input $\overline{S}$ and a 1 is entered on output Q. Current flows through light-emitting diode (LED) 1CR4 and thorugh R4 and R23 to ground. There is a 1 on plus input 5 of 1U1. Current flow through motor 155 is discontinued and the pump 93 stops pumping. The light in LED 1CR4 which is seen by the operator indicates the end of a count.

For normal operation of motor 155, the current through resistor R11 is no greater than a predetermined magnitude, typically 200 milliamperes. This magnitude is assumed for the purpose of explaining the operation of the apparatus shown in FIG. 6 in the case of excessive motor current. Based on this assumption, the voltage on pin 10 of 5U1 is about 0.3 V. If resistor R11 draws more than 200 ma., the voltage impressed on pin 9 of 5U1 through resistor R12 exceeds 0.3 volts and there is a 0 at the output of 5U1 (pin 8) and on the $\overline{S}$ input of latch 2U3. There is a 1 on the Q output of 2U3 and on conductor 301, through diode 1CR1. Diode 1CR1 is enabled indicating overcurrent. There is a 1 on conductor 303 stopping motor 155. There is also a 1 on output terminal INH, inhibit. Oscillator OSC is disabled (FIG. 5) and the counting by U3 stops. The indication as to the counts before oscillator OSC was disabled is available and provides intelligence as to how long the sampler operated before the overcurrent occurred.

Three conditions cause the output of amplifier 6U1 (pin 14) to go to 0:

1. A decrease in the voltage of battery 33 below approximately 4.3 volts. This condition is monitored by the voltage divider including the resistors R18, R19, R20. Normally these resistors impress more than 2.6 volts on pin 12 of 6U1. If the battery voltage drops below about 4.3 volts, the voltage on pin 12 drops below 2.6, the output of 6U1 goes to 0 and latch 4U3 is set. LED, 1CR2 is enabled and a 1 is impressed on conductor 301, conductor 303 and output terminal INH stopping the motor 155 and disabling the oscillator OSC.

2. If Q1 is unable to supply sufficient current to satisfy the circuit requirements. For normal operation, the output of amplifier 4U1 (pin 7) i above 1.9 volts. Current flows through the emitter and base of Q1. The drop across diode 1CR5 is about 0.7 volts so that pin 12 of 6U1 is 2.6 volts (1.9+0.7). There is a 1 on the output of 6U1. IF the voltage at the output of 4U1 is below 1.9, 1CR5 conducts, drawing pin 12 of 6U1 below 2.6 volts and there is a 1 on output Q of latch 4U3 and on conductors 301 and 303 and on output INH stopping the motor 155 and oscillator OSC.

3. On the operation of pressure switch S3. In this case, pin 12 of 6U1 goes to 0, the output of 4U3 goes to 1 and the motor and oscillator are stopped.

The network R24–C8 is a delay network which prevents surges from tripping latch 4U3.

Latch 3U3 operates to reset the apparatus at the start of an operation. Normally the set input $\overline{S}$ is grounded and output Q is 1. At the start of an operation when power is first applied, capacitor C5 operates as a short and R goes to 0. The latch is reset and Q goes to 0. There is a 0 on conductors 305 and 307. Latches 1U3, 2U3 and 4U3 are reset and there is also a 0 on output $\overline{RES}$ resetting the timer.

At full battery voltage, i.e., 5.3, divider R18, R19, R20 impresses a higher voltage than a 2.6 on pin 2 of amplifier 7U1. The output of this amplifier goes to 0. When the test switch 1S2 is actuated, current flows through 1CR3 indicating that the battery is fully charged. There is also 5 volts on output TST, test. Through R8 (FIG. 5), 2½ volts is impressed on input LR of counter U3 enabling indicator U4.

While a preferred embodiment of this invention has been disclosed herein, many modifications thereof are feasible. This invention is not to be limited except insofar as is necessitated by the spirit of the prior art.

I claim:

1. A fluid sampler including a fluid channel having means for processing fluid, a pump for transmitting fluid through said fluid-processing means, a motor, connected to said pump, for driving said pump, power-supply means, a circuit, interconnecting said motor and power-supply means, for energizing said motor, said circuit including controllable current conducting means, connected in said circuit in series with said motor, and means, connected to said current conducting means, for controlling said current conducting means so that said current conducting means conducts the motor current, responsive continuously, as distinct from digitally, over the whole range of operation of said sampler, substantially only to the electrical loading of said motor as said loading is governed by the reaction between said fluid and said pump, and not to any pressure-actuable monitor, for continuously controlling said motor at any setting of said sampler by continuously adjusting the terminal voltage of said motor over said whole range so as to track the changes in the flow of fluid through said processing means to maintain the flow of fluid through said processing means substantially constant over said whole range.

2. The apparatus of claim 1 wherein the fluid channel includes a fluid filter of the type which as it filters the fluid increasingly impedes the flow of fluid through said channel and wherein the motor-controlling means controls the motor so as to maintain the flow of fluid substantially constant notwithstanding the increasing impedance to fluid flow introduced by said filter.

3. The sampler of claim 1 wherein the pump is of the diaphragm type.

4. A fluid sampler including a fluid channel having means for processing fluid, a pump for transmitting fluid through said fluid processing means, a motor, connected to said pump, for driving said pump, power-supply means, and a circuit interconnecting said motor and power-supply means for energizing said motor, said circuit including feedback means free of moving parts connected in series with said motor to conduct the motor current, responsive continuously, as distinct from digitally, over the whole range of operation of said sampler, substantially only to the loading of said motor as governed by the reaction between said fluid and pump, for continuously controlling said motor at any setting of said sampler by continuously adjusting the terminal voltage of said motor over said whole range so as to track the change in the flow of the fluid through said processing means to maintain the flow of fluid in said processing means substantially constant over said whole range.

5. The sampler as defined in claim 4 wherein the circuit comprises an operational amplifier having a predetemined gain, an output coupled to one terminal of the motor and an input coupled to the feedback means and to the power-supply means.

6. The sampler as defined in claim 5 wherein the power-supply means comprises a source of voltage, a voltage divider network for providing a predetermined reference potential from the source of voltage to the input of said operational amplifier and including variable resistor means for varying the predetermined reference potential.

7. The sampler as defined in claim 6 wherein the feedback means includes a motor-current-sensing means coupled between the terminal of the motor other than the one terminal of the motor and ground potential and currentfeedback means for coupling said other terminal of said motor to said input of said operational amplifier.

8. The sampler as defined in claim 7 further comprising a current amplifier connectng the output of the operational amplifier to the one terminal of the motor.

9. A fluid sampler including a fluid channel having means for processing fluid, a pump for transmitting fluid through said fluid-processing means, a motor, connected to said pump, for driving said pump, power-supply means, a circuit, interconnecting said motor and power-supply means for energizing said motor, said circuit including means, connected in said circuit responsive to the electrical loading of said motor, as said loading is governed by the reaction between said fluid and said pump, and not to any pressure-actuable monitor, for controlling said motor, so as to maintain the flow of fluid through said processing means substantially constant, said fluid channel including a suction channel at the inlet to said pump and an exhaust channel at the outlet to said pump, the said fluid sampler also including a pressure-actuable switch, in communication with said suction channel and said exhaust channel, said switch being responsive to the excess of vacuum in the suction channel or excessive pressure in the exhaust channel, to stop operation of the motor.

10. A fluid sampler including a fluid channel having means for processing fluid, a pump for transmitting fluid through said fluid-processing means, a motor, connected to said pump, for driving said pump, power-supply means, a circuit, interconnecting said motor and power-supply menas, for energizing said motor, said circuit including controllable current conducting means, connected in said circuit in series with said motor, and means, connected to said current conducting means, for controlling said current conducting means so that said current conducting means conducts the motor current, responsive continuously, as distinct from digitally, over the whole range of operation of said sampler, substantially only to the magnitude of the current conducted by said motor for continuously controlling said motor at any setting of said sampler by continuously adjusting the terminal voltage of said motor over said whole range so as to track the changes in the flow of fluid through said processing means to maintain the flow of fluid through said processing means substantially constant over said whole range.

11. Drive apparatus for a pump of a fluid sampler having means for processing a fluid, said pump transmitting fluid through said processing means, said drive apparatus including a motor to be connected to said pump for driving said pump, powersupply means having opposite first and second poles, an operational amplifier having an output, an output-inverting input and an output non-inverting input, means, connected to said power-supply means and to said output, for supplying current to said motor, said current flowing through said motor between a first terminal electrically nearest said first pole and a second terminal electrically more remote from said first pole, means, connected between said second terminal and said second pole, for producing a first potential dependent on the magnitude of the current through said motor, feedback means connected to said first terminal, for impressing, as a second potential, a large proportion of the potential between said first terminal of said motor and said second pole of said supply on one of said inputs, means, connected to said first-potential producing means, for impressing said first potential on the other input, means, connected to said other input, for impressing on said other input a third potential corresponding to the desired flow of fluid through said processing means, said first, second and third potential and said feedback means being so related that the output of said operational amplifier is the analog of the relationship between said first and third potentials at said other input, said operational amplifier to operate, under the influence of said first and third potentials to continuously maintain constant the flow of fluid through said processing means over the whole range of operation of said sampler.

12. The drive apparatus of claim 11 wherein the first-potential-producing means is a resistor connected between the second terminal of the motor and the second pole.

13. The drive apparatus of claim 11 wherein the first-potential-producing means is a resistor connected between the second terminal of the motor and the second pole and the second-potential-impressing means is a network including high-resistance means and lower-resistance means connected between the first terminal of the motor and the second pole of the power supply, the other input of the operational amplifier being connected to said first terminal of said motor through said high-resistance means, the resistor connected between the second terminal of the motor and the second pole being of low magnitude compared to said high-resistance means.

14. A fluid sampler including a fluid channel having means for processing fluid, a pump for transmitting fluid through said fluid processing means, a motor, connected to said pump, for driving said pump, power-supply means, and a circuit interconnecting said motor and power-supply means for energizing said motor, said circuit including feedback means free of moving parts, responsive continuously, as distinct from digitally, substantially only to the loading of said motor as governed by the reaction between said fluid and pump, for continuously controlling said motor so as to track the changes in the flow of the fluid through said processing means to maintain the flow of fluid in said processing means substantially constant; said circuit also comprising an operational amplifier having a predetermined gain, and also having an output coupled to one terminal of said motor and an input coupled to said feedback means and to said power-supply means;

said power-supply means comprising:
  (a) a source of voltage,
  (b) a voltage-divider network for providing a predetermined reference potential from said source of voltage to said input of said operational amplifier, and
  (c) said network including variable-resistor means for varying the predetermined reference potential;

said feedback means including:
  (d) a motor-current sensing means, coupled between said terminal of said motor other than said one terminal of said motor and ground potential; and
  (e) current-feedback means for coupling said other terminal of said motor to said input of said operational amplifier;

said sampler also comprising a current amplifier connecting the output of said operational amplifier to said one terminal of said motor; and said sampler also comprising a fault-detector circuit for detecting when said motor-energizing circuit is unable to compensate for pump-flow requirements, said fault-detector circuit comprising:
  (f) means for sensing the voltage output of said operational amplifier, and
  (g) means, responsive to said voltage-sensing means, for disabling said motor-energizing circuit and said pump when the voltage-output level reaches a predetermined level representing excessive motor current demand.

15. A sampler as defined in claim 14 wherein the means for sensing the voltage output of the operational amplifier comprise a diode in combination with a comparator and wherein the means for disabling the motor circuit in response to the sensing means comprises a logical gate.

16. A fluid sampler including a fluid channel having means for processing a fluid, a pump, connected to said channel, for transmitting fluid through said processing means, a motor, connected to said pump for driving said pump, power-supply means, a first circuit interconnecting said motor and said power-supply means, when enabled for energizing said motor, a timing counter, a second circuit interconnecting said counter and said power-supply means, when enabled, for energizing said counter to count, means, connected to said counter, for presetting a count in said counter, means, connected to said first and second circuits, for enabling said circuits to energize said motor to drive said pump and to energize said counter to count, and means, connected to said presetting means, for disabling said first circuit and said second circuit simultaneously after said counter has counted said preset count thereby to terminate the driving of said pump and the counting of said counter.

17. The sampler of claim 16 including also means, connected to the first circuit and to the second circuit, when actuated, for disabling both the said circuits on the presence of a condition in the sampler militating against reliable operation.

18. The sampler of claim 17 wherein the disabling means includes means, responsive to the current flow through the motor, for actuating said disabling means.

19. The sampler of claim 17 wherein the power-supply means includes a battery and wherein the disabling means includes means, responsive to the voltage of said battery, for actuating said disabling means when the voltage of said battery decreases below a predetermined magnitude.

20. The sampler of claim 17 wherein current is supplied to the motor from the power-supply means through a transistor and wherein the disabling means includes means, responsive to the capability of the transistor to conduct current, for actuating said disabling means when the current which said transistor is capable of conducting decreases below a predetermined magnitude.

21. The sampler of claim 17 wherein current is supplied to the motor through a transistor having a collector, an emitter and a base and wherein the disabling means includes means, responsive to the potential impressed to conduct current between the said emitter and said base, for actuating the disabling means when said impressed potential decreases below a predetermined magnitude.

22. The sampler of claim 17 wherein the fluid channel includes a suction channel at the inlet to the pump and an exhaust channel at the outlet to the pump and wherein the sampler also includes a pressure-acutable switch, in communication with said suction channel and with said exhaust channel, said switch being operable on an excess of vacuum in the suction channel or an excess of pressure in the exhaust channel, and wherein the disabling means includes means, responsive to the operation of said switch for actuating said disabling means.

23. A fluid sampler including a fluid channel having means for processing fluid, a pump for transmitting fluid through said fluid-processing means, a motor, connected to said pump, for driving said pump, power-supply means, a circuit, interconnecting said motor and power-supply means, for energizing said motor, said circuit including feedback means free of moving parts in series with said motor so as to conduct the motor current, responsive continuously, as distinct from digitally, over the whole range of operation of said sampler, substantially only to the magnitude of the current conducted by said motor for continuously controlling said motor at any setting of said sampler by continuously adjusting the terminal voltage of said motor over said whole range, so as to track the changes in the flow of fluid through said processing means to maintain the flow of fluid through said processing means substantially constant over said whole range.

24. A fluid sampler including a fluid channel having means for processing fluid, a pump for transmitting fluid through said fluid-processing means, a motor, connected to said pump, for driving said pump, power-supply means, a circuit, interconnecting said motor and power-supply means, for energizing said motor, said circuit including feedback means free of moving parts, responsive continuously, as distinct from digitally, substantially only to the magnitude of the current conducted by said motor for continuously controlling said motor so as to track the changes in the flow of fluid through said processing means to maintain the flow of fluid through said processing means substantially constant, said circuit also including means, connected in said circuit, for compensating for the variation of the resistance with temperature of the winding material of said motor.

25. Drive apparatus for a pump of a fluid sampler having means for processing a fluid, said pump transmitting fluid through said processing means, said drive apparatus including a motor to be connected to said pump for driving said pump, power-supply means having opposite first and second poles, an operational amplifier having an output, an output-inverting input and an output non-inverting input, means, connected to said power-supply means and to said output, for supplying current to said motor, said current flowing through said motor between a first terminal electrically nearest said first pole and a second terminal electrically more remote from said first pole, means, connected between said second terminal and said second pole, for producing a first potential dependent on the magnitude of the current flowing through said motor, feedback means connected to said first terminal, for impressing, as a second potential, a large proportion of the potential between said first terminal of said motor and said second pole of said supply on said non-inverting input, means, connected to said first-potential producing means, for impressing said first potential on said inverting input, means, connected to said inverting input, for impressing on said inverting input a third potential corresponding to the desired flow of fluid through said processing means, said first-potential producing means, said second-potential impressing means, and said third-potential impressing means, being so selected and so related that said operational amplifier operates, under the influence of said first and third potentials to continuously maintain constant the flow of fluid through said processing means over the whole range of operation of said processing means.

* * * * *